(12) United States Patent
Hofmann et al.

(10) Patent No.: US 6,592,884 B2
(45) Date of Patent: Jul. 15, 2003

(54) METHOD OF USING ALPHA-KETO ENAMINE DERIVATIVES AS INGREDIENTS AND PRODUCTS INCORPORATING SAME

(75) Inventors: Thomas Hofmann, Neufahrn (DE); Harald Ottinger, Munich (DE); Oliver Frank, Neufahrn (DE); Tomislav Soldo, Munich (DE); Christoph Cerny, La Conversion (CH); Fabien Robert, Divonne les Bains (FR); Imre Blank, Savigny (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/863,970

(22) Filed: May 23, 2001

(65) Prior Publication Data

US 2002/0022039 A1 Feb. 21, 2002

(30) Foreign Application Priority Data

May 23, 2000 (EP) ............................................. 00110886

(51) Int. Cl.⁷ .......................... A61K 7/00; A61K 31/33; A01N 43/64
(52) U.S. Cl. ......................... 424/401; 514/183; 514/359
(58) Field of Search .......................... 424/401; 514/183, 514/359

(56) References Cited

U.S. PATENT DOCUMENTS 4,022,920 A * 5/1977 Doornbos et al. .......... 426/533

FOREIGN PATENT DOCUMENTS

| GB | 1096427 | 12/1967 |
| JP | 07 242661 | 9/1995 |
| JP | 07-242661 | 9/1995 |

OTHER PUBLICATIONS

Galantay et al, "Synthetic studies Related to Cephalosporin C," J. Org. Chem., 1964, vol. 29, iss. 12, pp. 3560–3566.*
T. Acree et al, eds., "Flavor Science: Sensible Principles and Techniques," American Chemical Society, pp. 23–37, 1993.*
Ottinger et al, Systematic Studies on Structure and Physiological Activity of Cyclic–a–Keto Enamines, a Novel Class of "Cooling Compounds," J. Agric. Food Chem., 2001, 49, 5383–5390, published Nov. 6, 2001.*
Frank et al, "On the Influence of the Carbohydrate Moiety on Chromophore Formation during Food–Related Maillard Reactions of Pentoses, Hexoses, and Disaccharides," Helvetica Chimica Acta, 2000, 83, 3246–3261, published Dec. 2000.*

A. Huyghues–Despointes et al., Pyrolysis/GC/MS Analysis of 1-[2'-Carboxy)pyrrolidinyl]-1-deoxy-D-fructose (Proline Amadori Compound), J. Agric. Food Chem., vol. 42, No. 11, 2519–2524 (1994).

R. Tressl et al., "Formation of Pyrrolidines and Piperidines on Heating L–Proline with Reducing Sugars", J. Agric. Food Chem., vol. 33, No. 5, 924–928 (1985).

R. Tressl et al., "Formation of 2-(1-Pyrrolidinyl)-2-cyclopentenones and Cyclopent(b)azepin-8(1H)-ones as Proline Specific Maillard Products", J. Agric. Food Chem., vol. 33, No. 6, 1132–1137 (1985).

T. Doornbos, et al., "Amadori Compounds, Derived from 6–deoxy Sugars, as Flavor Precursors," Prog. Food Nutr. Sci., pp. 57–63, 1981 (with Abstract from Chem. Abs., 91(11), Abs. No. 84374t, Mar. 15, 1982)).

H. Ottinger, et al., "Characterization of Natural Cooling Compounds Formed from Glucose and L–Proline in Dark Malt by Application of Taste Dilution Analysis," J. Agric. Food chem., 49(3):1336–1344 (2001), publication date Feb. 10, 2001.

* cited by examiner

Primary Examiner—Sreeni Padmanabhan
Assistant Examiner—Michael A. Willis
(74) Attorney, Agent, or Firm—Winston & Strawn

(57) ABSTRACT

The present invention concerns the food, cosmetic and pharmaceutical compositions including a compound of general formula:

(A)

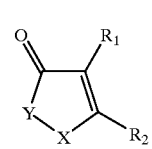

alone or in combination, as an ingredient for food, cosmetic, pharmaceutical, and perfume compositions, wherein $R_1$ includes N-Pyrrolidinyl, N-Pyridinyl, N-(amino-diethyl), N-(2-carboxy-pyrrolidinyl), N-(2-Methoxycarbonyl-pyrrolidinyl), or a combination thereof; $R_2$ includes hydrogen, methyl, or a combination thereof; X includes methylene, ethylidene, 1-Propylidene, oxy radical, or a combination thereof; and Y includes methylene, ethylidene, 1-propylidene, oxy radical, ethan-1,2-diyl, ethen-1,2-diyl, propan-1,2-diyl, ethan-1,2-oxy-1,2-yl, or a combination thereof. Food products containing such compositions, as well as methods of imparting a cooling effect on a consumer's skin, are also included.

19 Claims, No Drawings

METHOD OF USING ALPHA-KETO ENAMINE DERIVATIVES AS INGREDIENTS AND PRODUCTS INCORPORATING SAME

FIELD OF THE INVENTION

The present invention concerns the use of alpha-keto enamine derivatives as ingredients.

BACKGROUND OF THE INVENTION

The Maillard reaction of L-proline with reducing monosaccharides has been extensively studied during the last two decades in order to gain insights into the formation of volatiles during thermal processing of cereal products (Tressl et al., *J. Agric. Food Chem.* 1985a, 33, 919–923; Tressl et al. *J. Agric. Food Chem.* 1985b, 33, 924–928; Tressl et al. *J. Agric. Food Chem.* 1985c, 33, 1132–1137; Helak et al. *J. Agric. Food Chem.* 1989a, 37, 400–404; Helak et al. *J. Agric. Food Chem.* 1989b, 37, 405–410; Huyghues-Despointes et al. *J. Agric. Food Chem.* 1994, 42, 2519–2524).

By application of the GC/olfactometry techniques such as Charm analysis (Roberts, D. D., Acree, T. In *Thermally Generated Flavors;* Parliment T. H., Morello M. J., McGorrin R., Eds.; ACS, Washington DC, 1994, 71–79) or aroma extract dilution analysis (AEDA)(Hofmann, T., Schieberle, P. *J. Agric. Food Chem.* 1998, 46, 2721–2726), the odor-active compounds could be successfully detected in solvent extracts of Maillard reaction systems composed of L-proline and reducing sugars. Amongst the volatiles detected, the popcorn-like smelling compounds 2-acetyl-1-pyrroline and 2-acetyltetrahydropyridine could be identified as the key contributors to the overall odor of thermally processed glucose/proline mixtures (Hofmann and Schieberle, *J. Agric. Food Chem.* 1998, 46, 2270–2277). Although the major part of the volatile reaction products formed during these roasting processes could be unequivocally shown by AEDA to have no odor activity, it cannot be excluded that some of these odorless compounds might evoke a certain taste sensation on the tongue such as, e.g., bitterness, heating or cooling. Consequently, the sensory attributes of such reaction products from reducing carbohydrates and proline were characterized.

By application of the recently developed taste dilution analysis (Hofmann, T. *J. Agric. Food Chem.* 1999, 47, 4763–4768) on HPLC fractions obtained from roasted glucose/proline mixtures two compounds could be detected, which showed an intense cooling effect on the tongue. These compounds were found to be formed in high concentrations when the hexose degradation product 2-hydroxy-3-methyl-2-cyclopenten-1-one was reacted in the presence of L-proline. After isolation by column chromatography both compounds could be obtained as pale-yellow oils with a purity of more than 99%. GC/MS and 1D- and 2D-NMR spectroscopy led to the unequivocal identification of these cooling compounds as 5-methyl-2-(1-pyrrolidinyl)-2-cyclopenten-1-one (5-MPC) and 3-methyl-2-(1-pyrrolidinyl)-2-cyclopenten-1-one (3-MPC).

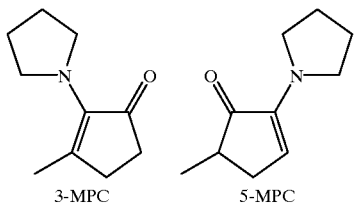

Although these compounds have been reported earlier by Tressl et al. (1985c) and Huyghues-Dispointes et al. (1994), these authors did not report on the cooling activity of these compounds when contacted with the tongue.

Besides 3-MPC and 5-MPC, we identified another cooling-active compound in the glucose/proline mixture, namely 2,5-dimethyl-4-(1-pyrrolidinyl)-3(2H)-furanone (DMPF).

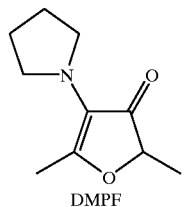

3-MPC as well as 5-MPC could easily be synthesised by heating 2-hydroxy-3-methyl-2-cyclopenten-1-one and pyrrolidinium acetate in ethanolic solution or by dry-heating of 2-hydroxy-3-methyl-2-cyclopenten-1-one in the presence of proline. In analogy, DMPF could be obtained by reacting 4-hydroxy-2,5-dimethyl-3(2H)-furanone in the presence of pyrrolidinium acetate in ethanol or in the presence of proline under dry-heating conditions, respectively.

Japanese Patent 7242661 discloses DMPF as flavoring compound to impart flavour to wheat flour foods. This patent concerns flavor emitted from such foods that were just heated. Hence the patent deals with DMPF as a flavour precursor. GB Patent No. 1096427 concerns certain cyclopentanone derivatives as interesting compounds for perfumery. Certain alpha-keto enamines are claimed, but they are mentioned only as intermediates for the synthesis of other compounds.

Thus, it is desired to obtain an improved cooling agent, particularly for use as an ingredient in foodstuffs.

SUMMARY OF THE INVENTION

The invention relates to a food, cosmetic, or pharmaceutical composition including a compound of the general formula:

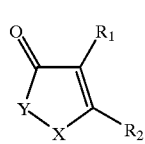

wherein $R_1$ includes N-Pyrrolidinyl, N-Pyridinyl, N-(amino-diethyl), N-(2-carboxy-pyrrolidinyl), N-(2-Methoxycarbonyl-pyrrolidinyl), or a combination thereof; $R_2$ includes hydrogen, methyl, or a combination thereof; X includes methylene, ethylidene, 1-Propylidene, oxy radical, or a combination thereof; and Y includes methylene, ethylidene, 1-propylidene, oxy radical, ethan-1,2-diyl, ethen-1,2-diyl, propan-1,2-diyl, ethan-1-oxy-1-yl, or a combination thereof.

In a first embodiment, $R_1$ includes N-pyrrolidinyl, $R_2$ includes hydrogen, X includes methylene and Y includes ethylidene. In a second embodiment, $R_1$ includes N-pyrtolidinyl, $R_2$ includes methyl, X includes oxy radical and Y includes methylene. In a third embodiment, $R_1$ includes N-Pyrrolidinyl, $R_2$ includes methyl, X includes methylene and Y includes oxy radical. In a fourth embodiment, $R_1$ includes N-Pyrrolidinyl, $R_2$ includes methyl, X includes ethylidene and Y includes oxy radical. In a preferred embodiment, the compound includes at least one of 3-Methyl-2-(1-pyrrolidinyl)-2-cyclopenten-1-one (3-MPC), 5-Methyl-2-(1-pyrrolidinyl)-2-cyclopenten-1-one (5-MPC), 3-Methyl-2-(1-piperidinyl)-2-cyclopenten-1-one (3-MPipC), 5-Methyl-2-(1-piperidinyl)-2-cyclopenten-1-one (5-MPipC), 3-Methyl-2-diethylamino-2-cyclopenten-1-one (3-MDeaC), 5-Methyl-2-diethylamino-2-cyclopenten-1-one (5-MDeaC), 3-Methyl-2-diethylamino-2-cyclopenten-1-one (3-MDeaC), 5-Methyl-2-diethylamino-2-cyclopenten-1-one (5-MDeaC), 3-Methyl-2-(2-carboxy-1-pyrrolidinyl)-2-cyclopentene-1-one (3-MProC), 5-Methyl-2-(2-methoxycarbonyl-1-pyrrolidinyl)-2-cyclopentene-1-one (5-MMeproC), 5-Ethyl-2-(1-pyrrolidinyl)-2-cyclopenten-1-one (5-EPC), 3,5-Dimethyl-2-(1-pyrrolidinyl)-2-cyclopenten-1-one (3,5-DMPC), 3,4-Dimethyl-2-(1-pyrrolidinyl)-2-cyclopenten-1-one (3,4-DMPC), 4,5-Dimethyl-2-(1-pyrrolidinyl)-2-cyclopenten-1-one (4,5-DMPC), 3-Methyl-2-(1-pyrrolidinyl)-2-cyclohexen-1-one (3-MPCH), 6-Methyl-2-(1-pyrrolidinyl)-2-cyclohexen-1-one (6-MPCH), 2,5-Dimethyl-4-(1-pyrrolidinyl)-3(2H)-furanone (DMPF), 5-Methyl-4-(1-pyrrolidinyl)-3(2H )-furanone (MPF), 4,5-Dimethyl-3-(1-pyrrolidinyl)-2(5H)-furanone (2(5H)-DMPF), 4-Methyl-3-(1-pyrrolidinyl)-2(5H)-furanone (2(5H)-MPF). In a more preferred embodiment, the compound includes 2,5-Dimethyl-4-(1-pyrrolidinyl)-3(2H)-furanone, 4,5-Dimethyl-3-(1-pyrrolidinyl)-2(5H)-furanone, 4-Methyl-3-(1-pyrrolidinyl)-2(5H)-furanone, or a combination thereof.

In one embodiment, the food composition includes at least one of chocolate, ice-cream, beverages, sugar confectionery, or petfood. In another embodiment, the cosmetic composition includes a topically administered cosmetic composition. In yet another embodiment, the perfume composition includes alcohol or water, or both. In any of these embodiments, the amount of the compound of formula (A) alone or in combination includes from about 0.01 mg/kg to 3000 mg/kg of the total composition. In general, the compound of formula A is present in an amount sufficient to impart a cooling effect.

This cooling effect is preferably accomplished with little or no detectable odor. Thus, in one embodiment, the compound has a cooling threshold to odor threshold ratio less than that of menthol. In a preferred embodiment, the ratio is less than about 3.

The invention also relates to a food product including the compounds and compositions including such compounds. In a preferred embodiment, the composition is completely free of mint-odor and optionally includes a fruity or brown flavor or odor. In one embodiment, the food product is a confectionery product or a malted beverage.

In one embodiment, the invention relates to a cosmetic product including the composition, while in another embodiment the invention relates to a perfume including the composition of the invention.

The invention also relates to a method of cooling a consumer's skin or mouth by contacting an effective amount of the composition to the consumer's skin or mouth to provide a cooling effect.

DETAILED DESCRIPTION OF THE PREFERRED EMBODIMENTS

The present invention advantageously provides a group of compounds having excellent characteristics when used as an ingredient, more particularly as a cooling agent in foods, cosmetics, or perfumes. In contrast to menthol, which exhibits a strong mint-like odor, the compounds of the invention possess no—or at most a faint—odor and do not substantially modify the aroma of a food or other compositions in which they are included. The compounds of the invention include those of the general formula:

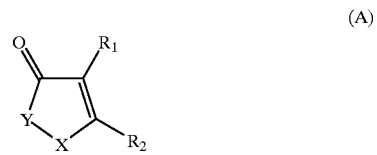

(A)

alone or in combination, as an ingredient for food, cosmetic, pharmaceutical and perfume compositions, wherein $R_1$ includes N-Pyrrolidinyl, N-Pyridinyl, N-(amino-diethyl), N-(2-carboxy-pyrrolidinyl), N-(2-Methoxycarbonyl-pyrrolidinyl), or a combination thereof. $R_2$ includes hydrogen, methyl, or a combination thereof. X includes methylene, ethylidene, 1-Propylidene, oxy radical, or a combination thereof. Y includes methylene, ethylidene, 1-Propylidene, oxy radical, ethan-1,2-diyl, ethen-1,2-diyl, propan-1,2-diyl, ethan-1-oxy-1-yl, or a combination thereof.

In the present specification, "alone" means that only one compound of general formula (A) can be used. But, it is also possible according to the invention, to use several different types of compounds of general formula (A) in the same composition.

In a first preferred embodiment, $R_1$ includes N-Pyrrolidinyl, $R_2$ includes hydrogen, X includes methylene and Y includes ethylidene (5-MPC). In a second preferred embodiment, $R_1$ includes N-Pyrrolidinyl, $R_2$ includes Methyl, X includes Oxy radical and Y includes methylene (MPF). In a third preferred embodiment, $R_1$ includes N-Pyrrolidinyl, $R_2$ includes methyl, X includes methylene and Y includes Oxy radical (4-methyl-3-(1-pyrrolidinyl)-2 (5H)-furanone, 2(5H)MPF). In a fourth preferred embodiment of the general compound of the invention, $R_1$ includes N-Pyrrolidinyl, $R_2$ includes methyl, X includes ethylidene and Y includes Oxy radical (4,5-dimethyl-3-(1-pyrrolidinyl)-2(5H)-furanone, 2(5H)DMPF). Preferred compounds of the invention include at least one of 3-Methyl-2-(1-pyrrolidinyl)-2-cyclopenten-1-one (3-MPC), 5-Methyl-2-(1-pyrrolidinyl)-2-cyclopenten-1-one (5-MPC), 3-Methyl-2-(1-piperidinyl)-2-cyclopenten-1-one (3-MPipC), 5-Methyl-2-(1-piperidinyl)-2-cyclopenten-1-one (5-MPipC), 3-Methyl-2-diethylamino-2-cyclopenten-1-one (3-MDeaC), 5-Methyl-2-diethylamino-2-cyclopenten-1-one (5-MDeaC), 3-Methyl-2-diethylamino-2-cyclopenten-1-one (3-MDeaC), 5-Methyl-2-diethylamino-2-cyclopenten-1-one (5-MDeaC), 3-Methyl-2-(2-carboxy-1-pyrrolidinyl)-2-cyclopentene-1-one (3-MProC), 5-Methyl-2-(2-methoxycarbonyl-1-pyrrolidinyl)-2-cyclopentene-1-one (5-MMeproC), 5-Ethyl-2-(1-pyrrolidinyl)-2-cyclopenten-1-one (5-EPC), 3,5-Dimethyl-2-(1-pyrrolidinyl)-2-cyclopenten-1-one (3,5-DMPC), 3,4-Dimethyl-2-(1-pyrrolidinyl)-2-cyclopenten-1-one (3,4-DMPC), 4,5-Dimethyl-2-(1-pyrrolidinyl)-2-cyclopenten-1- one (4,5-DMPC), 3-Methyl-2-(1-pyrrolidinyl)-2-cyclohexen-1-one (3-MPCH), 6-Methyl-2-(1-pyrrolidinyl)-2-cyclohexen-1-one (6-MPCH), 2,5-Dimethyl-4-(1-pyrrolidinyl)-3(2H)-furanone (DMPF), 5-Methyl-4-(1-pyrrolidinyl)-3(2H)-furanone (MPF), 4,5-Dimethyl-3-(1-pyrrolidinyl)-2(5H)-furanone (2(5H)-DMPF), 4-Methyl-3-(1-pyrrolidinyl)-2(5H)-furanone (2(5H)-MPF).

In the case of a food composition, preferred foods include chocolate, ice-cream, beverages, sugar confectionery, and petfood.

In the case of a cosmetic composition, the compounds can be used in any topically applied cosmetic compositions.

In the case of a perfume composition, the compounds of the invention can be used in alcohol-based or aqueous-based compositions.

The amount of the compound of general formula (A), alone or in combination, is from about 0.01 mg/kg to 3000 mg/kg, of the composition. In one embodiment, the amount of compound is from about 0.05 to 500 mg/kg, while in another embodiment, the amount of compound is from 01. to 50 mg/kg. As already mentioned above, the above mentioned compounds of general formula (A) are used for the cooling effect they can induce to the compositions where they are introduced.

General Procedure to Synthesize Compounds of Formula (A)

An ethanolic solution (e.g., 600 mL) of a cyclic enolone compound (e.g., 100 mmol) may be refluxed in the presence of equimolar amounts (e.g., 400 mmol) of an amino compound (e.g., pyrrolidine) and acetic acid for several hours (e.g., 1–5 h). After cooling to room temperature, the solvent may be removed in vacuo and the residue may be taken up in water. The pH may be adjusted to 10 with a sodium hydroxide solution (e.g., 30% in water). The solution may then be extracted with an organic solvent (e.g. diethyl ether), the combined organic layers washed with an aqueous solution of sodium carbonate (e.g., 200 mL; 0.5 mol/L), dried over sodium sulphate and then freed from solvent in vacuo. The target compounds may further be purified by column chromatography on aluminium oxide (basic, activity III–IV, Merck, Darmstadt, Germany). Chromatography may be performed using various organic solvents in different ratios such as for example hexane (e.g., 200 ml), hexane/diethyl ether (e.g., 7:3, 400 ml), hexane/diethyl ether (e.g., 3:7, 400 ml), and diethyl ether (e.g., 400 ml). The fraction obtained with diethyl ether may be freed from solvent in vacuo affording the target compound. The compounds in Table 1 can be synthesized according to this general procedure.

TABLE 1

Cooling compounds of the invention synthesized

| Enolones | Amines | Target compounds |
|---|---|---|
| 2-Hydroxy-3-methyl-2-cyclopenten-1-one | Pyrrolidine | 3-Methyl-2-(1-pyrrolidinyl)-2-cyclopenten-1-one (3-MPC); 5-Methyl-2-(1-pyrrolidinyl)-2-cyclopenten-1-one (5-MPC) |
| 2-Hydroxy-3-methyl-2-cyclopenten-1-one | Piperidine | 3-Methyl-2-(1-piperidinyl)-2-cyclopenten-1-one (3-MPipC); 5-Methyl-2-(1-piperidinyl)-2-cyclopenten-1-one (5-MPipC) |
| 2-Hydroxy-3-methyl-2-cyclopenten-1-one | Diethyl-amine | 3-Methyl-2-diethylamino-2-cyclopenten-1-one (3-MDeaC); 5-Methyl-2-diethylamino-2-cyclopenten-1-one (5-MDeaC) |
| 2-Hydroxy-3-methyl-2-cyclopenten-1-one | L-Proline | 3-Methyl-2-(2-carboxy-1-pyrrolidinyl)-2-cyclopentene-1-one (3-MProC) |

TABLE 1-continued

Cooling compounds of the invention synthesized

| Enolones | Amines | Target compounds |
|---|---|---|
| 2-Hydroxy-3-methyl-2-cyclopenten-1-one | L-Proline methylester | 5-Methyl-2-(2-methoxycarbonyl-1-pyrrolidinyl)-2-cyclo-pentene-1-one (5-MMeproC) |
| 2-Hydroxy-3-ethyl-2-cyclopenten-1-one | Pyrrolidine | 5-Ethyl-2-(1-pyrrolidinyl)-2-cyclopenten-1-one (5-EPC) |
| 2-Hydroxy-3,5-dimethyl-2-cyclopenten-1-one | Pyrrolidine | 3,5-Dimethyl-2-(1-pyrrolidinyl)-2-cyclopenten-1-one (3,5-DMPC) |
| 2-Hydroxy-3,4-dimethyl-2-cyclopenten-1-one | Pyrrolidine | 3,4-Dimethyl-2-(1-pyrrolidinyl)-2-cyclopenten-1-one (3,4-DMPC); 4,5-Dimethyl-2-(1-pyrrolidinyl)-2-cyclopenten-1-one (4,5-DMPC) |
| 2-Hydroxy-3-methyl-2-cyclohexen-1-one | Pyrrolidine | 3-Methyl-2-(1-pyrrolidinyl)-2-cyclohexen-1-one (3-MPCH); 6-Methyl-2-(1-pyrrolidinyl)-2-cyclohexen-1-one (6-MPCH) |
| 2,5-Dimethyl-4-hydroxy-3(2H)-furanone | Pyrrolidine | 2,5-Dimethyl-4-(1-pyrrolidinyl)-3(2H)-furanone (DMPF) |
| 4-Hydroxy-5-methyl-3(2H)-furanone | Pyrrolidine | 5-Methyl-4-(1-pyrrolidinyl)-3(2H)-furanone (MPF) |
| 3-Hydroxy-4,5-dimethyl-2(5H)-furanone | Pyrrolidine | 4,5-Dimethyl-3-(1-pyrrolidinyl)-2(5H)-furanone(2(5H)-DMPF) |
| 3-Hydroxy-4-methyl-2(5H)-furanone | Pyrrolidine | 4-Methyl-3-(1-pyrrolidinyl)-2(5H)-furanone(2(5H)-MPF) |

Syntheses of 5-methyl-2-(1-pyrrolidinyl)-2-cyclopenten-1-one (5-MPC) and 3-methyl-2-(1-pyrrolidinyl)-2-cyclopenten-1-one (3-MPC)

1. From 2-hydroxy-3-methyl-2-cyclopenten-1-on (cyclotene) and pyrrolidinium acetate in ethanol A solution of cyclotene (100 mmol), pyrrolidine (400 mmol) and acetic acid (400 mmol) in ethanol (600 mL) was refluxed for 2 h. After cooling to room temperature, the solvent was removed in vacuo, the residue was taken up in water (300 mL) and the pH was adjusted to 10 with sodium hydroxide solution (30% in water). The solution was then extracted with diethyl ether (5×150 mL), the combined organic layers were washed with an aqueous solution of sodium carbonate (200 mL; 0.5 mol/L), dried over Na$_2$SO$_4$ and then freed from solvent in vacuo. The residual oil was dissolved in pentane/ethyl ether (6/4, v/v; 10 mL) and then applied onto a column (30×500 mm) filled with a slurry of aluminium oxide (basic, activity III–IV, Merck, Darmstadt, Germany) in pentane. Chromatography was performed using pentane (300 mL; fraction A), pentane/diethyl ether (9/1, v/v; 300 mL; fraction B), pentane/diethyl ether (8/2, v/v; 300 mL; fraction C), pentane/diethyl ether (7/3, v/v; 300 mL; fraction D), pentane/diethyl ether (6/4, v/v; 300 mL; fraction E), followed by pentane/diethyl ether (5/5, v/v; 300 mL, fraction F). Fraction B containing 5-MPC (1.65 g, 10% in yield) and fraction D containing 3-MPC (1.32 g, 8% in yield) were collected and freed from solvent under vacuum affording the target compounds as pale-yellow oils.

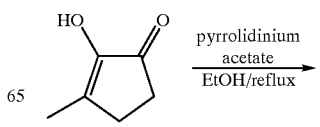

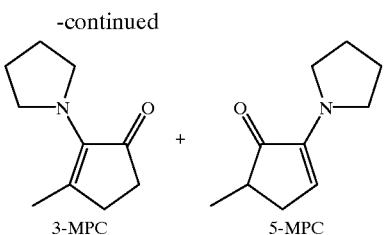

3-MPC + 5-MPC

Synthetic preparation of 3-methyl-2-(1-pyrrolidinyl)-2-cyclopentene-1-one (3-MPC) and 5-methyl-2-(1-pyrrolidinyl)-2-cyclopentene-1-one (5-MPC)

2. From 2-hydroxy-3-methyl-2-cyclopenten-1-on (cyclotene) and proline dry-heated on aluminium oxide. A mixture of cyclotene (100 mmol) and proline (100 mmol) was ground with aluminium oxide (20 g, basic, activity III–IV) and then dry-heated for 10 mm at 180° C. The mixture was suspended in water (100 mL) filtered, the pH was adjusted to 10 with sodium hydroxide solution (30% in water) and then extracted with diethyl ether. The work-up of the reaction mixture was performed following the procedure detailed above for the cyclotene/pyrrolidinium acetate mixture. The target compounds 5-MPC (120 mg) and 3-MPC (33 mg) were obtained as pale-yellow oils.

Spectroscopic Data

3-MPC:

MS (EI): 165 (100; [M]$^+$), 164 (47), 137 (34), 136 (38), 122 (53), 109 (136), 108 (43), 94 (27), 81 (26), 67 (21), 41 (27).

$^1$H NMR (360 MHz; CDCl$_3$, COSY, TOCSY): δ1.77–1.81 (m, 2×2H, CH$_2$), 2.13 (s, 3H, CH$_3$), 2.34–2.35 (m, 2H, CH$_2$), 2.39–2.41 (m, 2H, CH$_2$), 3.40–3.44 (m, 2×2H, CH$_2$).

$^{13}$C NMR (360 MHz; CDCl$_3$; DEPT, HMQC, HMBC): δ17.8 [CH$_3$], 24.9 [2×CH$_2$], 30.0 [CH$_2$], 34.1 [CH$_2$], 49.5 [2×CH$_2$], 143.7 [C], 145.9 [C], 205.9 [CO].

5-MPC:

MS (EI): 165 (100; [M]$^+$), 164 (32), 150 (26), 137 (22), 136 (37), 122 (87), 108 (34), 95 (34), 94 (31), 70 (21), 67 (24), 54 (24), 41 (25).

$^1$H NMR (360 MHz; CDCl$_3$, COSY, TOCSY): δ1.16–1.18 (d, 3H, J=7.5 Hz, CH$_3$), 1.82–1.88 (m, 2×2H, CH$_2$), 2.06–2.11 (dd, J=17.7, 2.2 Hz, 1H, CH$_a$H), 2.35–2.43 (m, 1H, J=7.5, 2.2; CH), 2.71–2.78 (dd, J=17.7, 3.1 Hz, 1H, CHH$_b$), 3.22–3.33 (m, 2×2H, CH$_2$), 5.82–5.83 (t, J=3.1 Hz, 1H, CH).

$^{13}$C NMR (360 MHz; CDCl$_3$; DEPT, HMQC, HMBC): δ16.5 [CH$_3$], 24.8 [2×CH$_2$], 32.6 [CH$_2$], 40.2 [CH], 48.1 [2×CH$_2$], 123.6 [CH], 146.7 [C], 207.4 [CO].

Synthesis of 5-methyl-4-(1-pyrrolidinyl)-3(2H)-furanone (MPF)

1. From xylose and pyrrolidine. A solution of xylose (0.1 mol) and pyrrolidine (0.1 mol) in methanol (90 ml) was refluxed for 3 h, then, acetic acid (0.1 mol) was added and heating was continued for additional 2 h. After cooling, the solvent was removed in vacuo, the residue was taken up in water (100 ml), extracted with ethyl acetate (100 ml, 5 times), and the combined organic layers were extracted with aqueous 0.1M sodium hydroxide solution (3×50 ml), the organic phase was dried (sodium sulphate) and fractionated by column chromatography using aluminium oxide (basic, activity III–IV; Merck, Darmstadt, Germany) conditioned in n-hexane. Chromatography was performed using hexane (200 ml), followed by hexane/diethyl ether 7:3 (400 ml), 3:7 (400 ml), and diethyl ether (400 ml). The fraction obtained with diethyl ether was freed from solvent in vacuo affording the target compound MPF (0.9 mmol; 0.9%) as colorless oil with a purity of more than 99%.

2. From 4-hydroxy-5-methyl-3(2H)-furanone and pyrrolidine. A mixture of 4-hydroxy-5-methyl-2H-furan-3-one (10 mmol), pyrrolidine (20 mmol) and acetic acid (20 mmol) in methanol (50 ml) was refluxed for 3 h. After cooling, the solvent was removed in vacuo, the residue was taken up in H$_2$O (100 ml), extracted with ethyl acetate (100 ml, 5 times), and the combined organic layers were extracted with aqueous 0.1M sodium hydroxide solution (3×50 ml), the organic phase was dried (sodium sulphate) and fractionated by column chromatography as detailed above. The target compound MPF (0.5 mmol; 5% yield) was obtained as colorless oil with a purity of more than 99%.

Spectroscopic data of MPF

GC/MS (EI): 42 (100), 167 (95), 54 (93), 96 (76), 124 (74)

$^1$H NMR (360 MHz; CDCl$_3$, COSY, TOCSY): 1.82 (m, 2×2H, CH$_2$), 2.23 (s, 3H, CH$_3$), 3.11 (m, 2×2H, CH$_2$), 4.38 (s, 2H, CH$_2$)

$^{13}$C-NMR (360 MHz; CDCl$_3$): 14.2 (CH$_3$), 24.7 (2×CH$_2$), 50.6 (2×CH$_2$), 72.9 (CH$_2$), 126.3 (C), 183.0 (C), 198.9 (CO)

Syntheses of 4,5-Dimethyl-3-(1-pyrrolidinyl)-2(5H)-furanone [2(5H)DMPF]

1. From 3-Hydroxy-4,5-dimethyl-2(5H)-furanone and pyrrolidium acetate in ethanol. A solution of 3-hydroxy-4,5-dimethyl-2(5H)-furanone (10 mmol), acetic acid (10 mmol) and pyrrolidine (10 mmol) in ethanol (50 mL) were refluxed for 3 h. After cooling to room temperature, the solvent was removed in vacuo and the residue was taken up in water (25 mL). The solution was then extracted with diethyl ether (5×10 ml), the combined organic layers were dried over sodium sulfate and then freed from solvent in vacuo. The residual oil was dissolved in pentane/diethyl ether (4/1, v/v; 5 mL) and then applied onto a column (30×500 mm) filled with a slurry of aluminium oxide (basic, activity III–IV, Merck, Darmstadt, Germany) in pentane. Chromatography was performed using pentane (300 mL; fraction A), pentane/diethyl ether (9/1, v/v; 400 mL; fraction B), pentane/diethyl ether (80/20, v/v; 400 mL; fraction C), pentane/diethyl ether (70/30, v/v; 400 mL; fraction D), pentane/diethyl ether (60/40, v/v; 400 mL; fraction E). Fraction E containing 2(5H)-DMPF (0.64 g, 36% in yield) was collected and freed from solvent under vacuum affording the target compounds a colorless oil.

Spectroscopic Data of 2(5H)-DMPF

MS (EI): 181 (82; [M]$^+$), 166 (76), 138 (28), 136 (49), 122 (100), 110 (74), 108 (93), 94 (37), 82 (36), 68 (26), 55 (43), 54 (26), 53 (24), 43 (31), 41 (44).

$^1$H NMR (360 MHz; CDCl$_3$, COSY, TOCSY): δ1.35–1.36 (d, 3H, J=6.6 Hz, CH$_3$), 1.79–1.86 (m, 2×2H, CH$_2$), 2.03 (s, 3H, CH$_3$), 3.47–3.57 (m, 2×2H, CH$_2$), 4.66–4.72 (q, 1H, J=6.6 Hz, CH).

$^{13}$C NMR (360 MHz; CDCl$_3$; DEPT, HMQC, HMBC): δ11.8 [CH$_3$], 19.2 [CH$_3$], 24.9 [2×CH$_2$], 49.3 [2×CH$_2$], 78.0 [CH], 128.7 [C], 130.5 [C], 170.4 [CO].

Syntheses of 4-Methyl-3-(1-pyrrolidinyl)-2(5H)-furanone [2(5H)-MPF]

1. From 4-Methyl-dihydro-furan-2,3-dione and pyrrolidium acetate in ethanol. A solution of 4-methyl-dihydro-furan-2,3-dione (100 mmol, prepared according to Fleck et al., Helv. Chim. Acta 1950, 33, 130), acetic acid (100 mmol) and pyrrolidine (100 mmol) in ethanol (225 mL) was refluxed for 2,5 h. After cooling down to room temperature, the solvent was removed in vacuo and the residue was taken up in water (200 mL). The solution was then extracted with diethyl ether (5×100 ml), the combined organic layers were dried over sodium sulphate and then freed from solvent in vacuo. The residual oil was dissolved in pentane/diethyl ether (3/2, v/v; 10 mL) and then applied onto a column (30×500 mm) filled with a slurry of aluminium oxide (basic activity III–IV, Merck, Darmstadt, Germany) in pentane. Chromatography was performed using pentane (300 mL; fraction A), pentane/diethyl ether (9/1, v/v; 400 mL; fraction B), pentane/diethyl ether (80/20, v/v; 400 mL; fraction C), pentane/diethyl ether (70/30, v/v; 400 mL; fraction D), pentane/diethyl ether (60/40, v/v; 400 mL; fraction E), pentane/diethyl ether (50/50, v/v; 400 mL; fraction F). Fraction F containing 2(5H)-MPF (2.25 g, 14% in yield) was collected and freed from solvent under vacuo affording the target compound as a colorless oil.

Spectroscopic Data of 2(5H)-MPF

MS (El): 167 (94; [M]$^+$), 166 (63), 139 (58), 138 (45), 122 (93), 120 (43), 111 (54), 110 (46), 108 (32), 95 (26), 94 (100), 82 (25), 81 (24), 80 (23), 68 (67), 67 (21), 55 (36), 54 (27), 53 (23), 41 (58). $^1$H NMR (360 MHz; CDCl$_3$, COSY, TOCSY): δ1.80–1.86 (m, 2×2H, CH$_2$), 2.09 (s, 3H, CH$_3$), 3.49–3.54 (m, 2×2H, CH$_2$), 4.53 (s, 2H, CH$_2$). $^{13}$C NMR (360 MHz; CDCl$_3$; DEPT, HMQC, HMBC): δ12.4 [CH$_3$], 25.1 [2×CH$_2$], 49.5 [2×CH$_2$], 71.7 [CH$_2$], 124.3 [C], 130.7 [C], 171.6 [CO].

Sensory Analyses

Prior to sensory analysis, the purity of the synthetic taste compounds was checked by GC/MS. Determination of the cooling, as well as the aroma threshold, of the compounds was performed by trained panelists. Nasal odor thresholds (Guth, H.; Grosch, W. J. Am. Oil Chem. Soc. 1993, 70, 513–518), as well as cooling thresholds, were determined by triangle tests using tap water as the solvent. The samples were presented in order of increasing concentrations and the threshold values evaluated in three separate sessions were averaged. The values between individuals and separate sessions differed by not more than one dilution step.

The results of the sensory analyses are summarized in Table 2. Besides menthol, 5-MPC, 2(5H)-DMPF, MPF and 2(5H)-MPF had the lowest cooling threshold. Comparison of the odor threshold concentrations revealed the lowest value for menthol, which elicited a strong mint-like aroma, whereas the novel cooling agents showed significantly higher odor thresholds. Calculating the ratio of cooling threshold to odor threshold clearly demonstrated that the invention compounds, possessing no odor or only a faint odor, can be used as cooling compounds without imparting a strong odor. In comparison, for menthol the odor threshold is lower by a factor of 9.5, thereby, indicating that it is hardly possible to evoke a cooling effect in a product with menthol without having a significant mint-like odor. These data also show that by using the novel cooling compounds, it is now possible to evoke certain cooling effects during consumption of non-mint food compositions such as, confectionery products, malted beverages, and fruity or brown flavours. Especially 2(5H)-DMPF, MPF and 2(5H)-MPF have a much lower ratio of cooling threshold to odor threshold as compared to menthol and are, therefore, very efficient cooling substances.

TABLE 2

Comparison of cooling and odor thresholds of selected compounds

| Cooling substance | Cooling threshold[a] | Odor threshold[a] | Odor quality | Ratio (Cool/Odor) |
|---|---|---|---|---|
| 3-MProC | 490–735 | — | odorless | <<0.01 |
| 5-MMeproC | 112–188 | — | odorless | <<0.01 |
| DMPF | 100–140 | 30–60 | nutty, roasty | 2.7 |
| 3-MPCH | 90–150 | 45–75 | faintly mint-like | 2.0 |
| 4,5-DMPC | 68–113 | 136–226 | faintly mint-like | 0.5 |
| 3-MPipC | 60–100 | 80–120 | faintly amine-like | 0.8 |
| 3,4-DMPC | 51–86 | 26–43 | rubber-like | 2.0 |
| 3,5-DMPC | 33–54 | 16–27 | rubber-like | 2.0 |
| 3-MPC | 29–44 | 44–73 | faintly amine-like | 0.8 |
| 6-MPCH | 27–45 | 3.4–5.6 | rubber-like | 8.0 |
| 5-EPC | 27–43 | 13–22 | faintly mint-like | 2.0 |
| 5-MpipC | 16–24 | 12–20 | faintly mint-like | 2.7 |
| 5-MdeaC | 12–20 | 6.0–9.0 | curcuma-like | 2.1 |
| 5-MPC | 4.5–9 | 2.6–5.2 | faintly mint-like | 1.7 |
| 2(5H)-DMPF | 2.0–4.0 | 32–64 | faintly mint-like | 0.06 |
| MPF | 1.5–3.0 | — | odorless | <<0.01 |
| 2(5H)-MPF | 0.02–0.06 | — | odorless | <<0.01 |
| (-)-Menthol | 0.9–1.9 | 0.1–0.2 | mint-like | 9.5 |

[a]Threshold values [mg/kg] determined in water.

In an additional experiment, the cooling thresholds of 3-MPC, 5-MPC, MPF, 2(5H)-MPF and 2(5H)-DMPF have been determined in chocolate. As given in Table 3, also in chocolate, 2(5H)-MPF was evaluated with the lowest cooling threshold of about 0.25 mg/100 g to 0.5 mg/100 g, whereas the 5-MPC showed an 8-fold higher cooling threshold. The ratio for compounds of the invention is typically less than that of menthol, preferably less than 9, more preferably less than about 3. In other embodiments, the cooling threshold to odor threshold ratio is less than about 1 or less than about 0.1.

TABLE 3

Cooling thresholds of MPF, 3-MPC and 5-MPC in milk chocolate

| Cooling compound | Cooling effect [mg/100 g chocolate] |
|---|---|
| 2(5H)-MPF | 0.25–0.5 |
| MPF | 0.8–1.5 |
| 5-MPC | 2.3–3.7 |
| 2(5H)-DMPF | 5.0–7.5 |
| 3-MPC | 38–63 |

Identification of 5-methyl-2-(1-pyrrolidinyl)-2-cyclopenten-1-one (5-MPC), 3-methyl-2-(1-pyrrolidinyl)-2-cyclopenten-1-one (3-MPC) and 2,5-dimethyl-4-(1-pyrrolidinyl)-3(2H)-furanone (DMPF) in Roasted Malt Dark malt (50 g, Caraffa special) was frozen in liquid nitrogen and then ground in a mortar. The powder was then stirred overnight with dichloromethane (2×400 mL). The combined organic layers were then concentrated to about 50 mL in vacuo and the volatile fraction of the malt components were then isolated by high-vacuum distillation at 25° C. The distillate obtained was concentrated to about 1 mL and then fractionated by column chromatography (0.9×100 mm) on aluminium oxide (basic, activity III–IV, Merck, Darmstadt, Germany), which was conditioned in pentane. Chromatography was performed using pentane (100 mL; fraction A), pentane/diethyl ether (9/1, v/v; 100 mL; fraction B), pentane/diethyl ether (8/2, v/v; 100 mL; fraction C), pentane/diethyl ether (7/3, v/v; 100 mL; fraction D), pentane/diethyl ether (6/4, v/v; 100 mL; fraction E), pentane/diethyl ether (4/6, v/v; 100 mL; fraction F), pentane/diethyl ether (2/8, v/v; 100 mL; fraction G), followed by diethyl ether (100 mL, fraction H). Fraction B, fraction D and fraction G, respectively, were collected and analysed by GC/MS. By comparison of the retention times as well as mass spectra (EI, CI) with those obtained from the synthetic reference compounds, 5-MPC (101.3 μg/Kg) could be identified in fraction B, 3-MPC (9.4 μg/Kg) in fraction D and DMPF (11.5 μg/Kg) in fraction G.

EXAMPLES

These and other aspects of the present invention may be more fully understood with reference to the following non-limiting examples, which are merely illustrative of the preferred embodiments of the present invention, and are not to be construed as limiting the invention, the scope of which is defined by the appended claims.

Example 1

Application of 5-methyl-2-(1-pyrrolidinyl)-2-cyclopenten-1-one (5-MPC) and 5-methyl-4-(1-pyrrolidinyl)-3(2H)-furanone (MPF) in Mineral Water Solutions of 10% 1-menthol, 10% 5-MPC and 10% MPF, respectively, in ethanol were diluted with Vittel™ mineral water. The solutions were tasted and compared with pure Vittel™ water.

| Sample | | Flavor |
|---|---|---|
| Vittel ™ | | Neutral in aroma and taste |
| 1-Menthol in Vittel ™ | (10 mg/L) | Pronounced cooling effect, strong mint-like odor |
| 5-MPC in Vittel ™ | (100 mg/L) | Pronounced cooling effect with a slight mint-like odor |
| MPF in Vittel ™ | (400 mg/L) | Pronounced cooling effect, neutral in aroma |

Example 2

Application of 5-MPC and MPF in Orange Juice

Several cooling substances were evaluated in orange juice. 1-Menthol contributed with a strong cooling effect at 20 mg/L. It showed also a strong mint-like aroma, thus disbalancing the overall flavour of the fruit juice. The new cooling compound 5-MPC, added at 200 mg/L, exhibited also a strong cooling effect. In addition to its cooling effect, it exhibited a weak mint-like herbal aroma note, which was however less pronounced than with 1-menthol. The addition of 1000 mg/L MPF to orange juice caused a pronounced cooling effect in the mouth cavity without any additional aroma sensation. Hence, MPF is suitable to add a cooling effect to orange juice without changing the aroma profile, contrary to 1-menthol.

Example 3

Application of 5-MPC and MPF in Sugar Confectionery

Sugar (100 g) was heated together with water (15 g) in a beaker on a hot plate. After the mixture became a clear solution, the sugar syrup was heated further until it became viscous due to the evaporation of water. Then 5-MPC (20 mg) and MPF (100 mg), respectively, were added. The viscous liquid was then poured into molds (3 g each) and cooled down to room temperature. The candies, which had been formed in the molds, were demolded and used for taste testing. Both candies with 5-MPC and MPF, respectively, had a pronounced cooling effect in the mouth, compared with a reference without cooling substance. The candies with MPF showed no additional flavour quality and were preferred to those with 5-MPC, which were slightly oily and mint-like.

Example 4

Application of 5-MPC in Ice Cream

Full-fat cream (250 g), milk (250 ml) and sugar (100 g) were mixed and stirred until the sugar was dissolved. Then the mixture was poured into an ice cream machine (II Gelataio Super, Simac Inc., Gessate, Italy) and frozen within 30 minutes while stirring. In the same way, ice cream was prepared with 5-MPC (20 mg/kg). The ice cream with 5-MPC showed a pronounced long lasting cooling effect. The cool refreshing impression of this ice cream persisted much longer than with the unflavored reference compound.

Example 5

Topical Testing of 5-MPC, 2(5H)-DMPF, 2(5H)-MPF and MPF

Topical thresholds of cooling compounds 5-MPF, 2(5H)-DMPF, 2(5H)-MPF and MPF were determined as follows: An aliquot (0.5 mL) of a solution, containing 0.05, 0.1, 0.2, 0.5, or 1.0% of the coolant in water, was applied to a circular area (10 $cm^2$) of the skin surface on the inside of the right forearm, midway between the wrist and the elbow, and were rubbed for 1 min. In parallel, an aliquot (0.5 mL) of pure tap water was applied as the blank onto the skin of the left forearm. After 1 min, the skin was dried. A panel of 10 subjects (male and female) were asked to rank the cooling intensity on a scale from 0 (no effect) to 5 (very strong). The values evaluated in three different sessions at two days were averaged. The values between individuals and separate sessions differed not more than 2 scores.

| Topical testing of 5-MPC and MPF on the inside of the forearm | | | | |
|---|---|---|---|---|
| | Cooling intensity of[a] | | | |
| Concentration [%] | 2(5H)-MPF | 2(5H)-DMPF | MPF | 5-MPC |
| 0.00020 | 0 | | 0 | 0 |
| 0.00039 | 1 | | 0 | 0 |
| 0.00078 | 2 | | 0 | 0 |
| 0.00156 | 3 | | 0 | 0 |
| 0.00313 | 5 | | 0 | 0 |
| 0.00625 | 5 | 0 | 0 | 0 |
| 0.0125 | n.d. | 1 | 0 | 0 |
| 0.025 | n.d. | 3 | 0 | 0 |
| 0.05 | n.d. | 5 | 1 | 0 |
| 0.1 | n.d. | 5 | 2 | 0 |
| 0.2 | n.d. | 5 | 4 | 1 |
| 0.5 | n.d. | 5 | 5 | 3 |
| 1.0 | n.d. | 5 | 5 | 5 |

[a]Cooling effect on skin was determined in tap water by using a topicl test scoring the cooling intensity on a scale from 0 (no effect) to 5 (very strong). n.d. means cooling effect not detected.

Although preferred embodiments of the invention have been illustrated in the accompanying drawings and described in the foregoing Detailed Description, it will be understood that the invention is not limited to the embodiments disclosed, but is capable of numerous rearrangements and modifications of parts and elements without departing from the spirit of the invention. It will be understood that the mechanical and chemical details of every embodiment may be slightly different or modified by one of ordinary skill in the art without departing from the present invention.

What is claimed is:

1. A food, cosmetic, perfume, or pharmaceutical composition comprising one or more compounds each of the general formula:

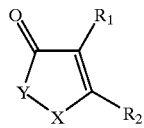

(A)

wherein $R_1$ is N-Pyrrolidinyl, $R_2$ is methyl, X is ethylidene and Y is oxy radical.

2. The composition of claim 1, wherein the composition further comprises a compound wherein $R_1$ is N-pyrrolidinyl, $R_2$ is methyl, X is oxy radical and Y is methylene.

3. The composition of claim 1, wherein the composition further comprises at least one of 3-Methyl-2-(1-piperidinyl)-2-cyclopenten-1-one (3-MPipC), 5-Methyl-2-(1-piperidinyl)-2-cyclopenten-1-one (5-MPipC), 3-Methyl-2-diethylamino-2-cyclopenten-1-one (3-MDeaC), 5-Methyl-2-diethylamino-2-cyclopenten-1-one (5-MDeaC), 3-Methyl-2-(2-carboxy-1-pyrrolidinyl)-2-cyclopentene-1-one (3-MProC), 5-Methyl-2-(2-methoxycarbonyl-1-pyrrolidinyl)-2-cyclo-pentene-1-one (5-MMeproC), 5-Ethyl-2-(1-pyrrolidinyl)-2-cyclopenten-1-one (5-EPC), 3,5-Dimethyl-2-(1-pyrrolidinyl)-2-cyclopenten-1-one (3,5-DMPC), 3,4-Dimethyl-2-(1-pyrrolidinyl)-2-cyclopenten-1-one (3,4-DMPC), 4,5-Dimethyl-2-(1-pyrrolidinyl)-2-cyclopenten-1-one (4,5-DMPC), 3-Methyl-2-(1-pyrrolidinyl)-1-cyclohexen-1-one (3-MPCH), 6-Methyl-2-(1-pyrrolidinyl)-2-cyclohexen-1-one (6-MPCH), 2,5-Dimethyl-4-(1-pyrrolidinyl)-3(2H)-furanone (DMPF), 5-Methyl-4-(1-pyrrolidinyl)-3(2H)-furanone (MPF), or 4,5-Dimethyl-3-(1-pyrrolidinyl)-2(5H)-furanone (2(5H)-DMPF).

4. The composition of claim 1, wherein the composition further comprises 2,5-Dimethyl-4-(1-pyrrolidinyl)-3(2H)-furanone, 4,5-Dimethyl-3-(1-pyrrolidinyl)-2(5H)-furanone, or a combination thereof.

5. The composition of claim 1, wherein the food composition comprises at least one of chocolate, ice-cream, beverages, sugar confectionery, or petfood.

6. The composition of claim 1, wherein the cosmetic composition comprises a topically administered cosmetic composition.

7. The composition of claim 1, wherein the perfume composition comprises an alcohol or water.

8. The composition of claim 6, wherein the amount of the compound of formula (A) alone or in combination comprises from about 0.01 mg/kg to 3000 mg/kg of the total composition.

9. The composition of claim 1, wherein the compound of formula A is present in an amount sufficient to impart a cooling effect.

10. The composition of claim 1, wherein the compound has a cooling threshold to odor threshold ratio less than that of menthol.

11. The composition of claim 10, wherein the ratio is less than about 3.

12. A food product comprising the composition of claim 1.

13. The food product of claim 12, wherein the composition is completely free of mint-odor.

14. The food product of claim 13, comprising a confectionery product or a malted beverage.

15. A cosmetic product comprising the composition of claim 1.

16. A perfume comprising the composition of claim 1.

17. A method of cooling a consumer's skin or mouth which comprises contacting an effective amount of a food, cosmetic, perfume, or pharmaceutical composition to the consumer's skin or mouth to provide a cooling effect, wherein the composition comprises one or more compounds each of the general formula:

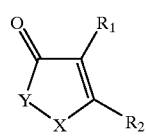

(A)

wherein $R_1$ is selected from the group consisting of N-Pyrrolidinyl, N-Pyridinyl, N-(amino-diethyl), N-(2-carboxy-pyrrolidinyl), piperidinyl, or N-(2-Methoxycarbonyl-pyrrolidinyl); $R_2$ is selected from the group consisting of hydrogen or methyl; X is selected from the group consisting of methylene, ethylidene, 1-Propylidene, or oxy radical; and Y is selected from the group consisting of methylene, ethylidene, 1-propylidene, oxy radical, ethan-1,2-diyl, ethen-1,2-diyl, propan-1,2-diyl, or ethan-1-oxy-1-yl, provided that when $R_1$ is N-pyrrolidinyl, X is methylene, and Y is ethylidene then $R_2$ cannot be hydrogen, and provided that when $R_1$ is N-pyrrolidinyl, and X and Y are each methylene, then $R_2$ cannot be methyl.

18. The method of claim 17, wherein $R_1$ is N-Pyrrolidinyl, $R_2$ is methyl, X is methylene and Y is oxy radical.

19. The method of claim 17, wherein $R_1$ is N-Pyrrolidinyl, $R_2$ is methyl, X is ethylidene and Y is oxy radical.

* * * * *

UNITED STATES PATENT AND TRADEMARK OFFICE
CERTIFICATE OF CORRECTION

PATENT NO.   : 6,592,884 B2
DATED        : July 15, 2003
INVENTOR(S)  : Hofmann et al.

It is certified that error appears in the above-identified patent and that said Letters Patent is hereby corrected as shown below:

<u>Title page,</u>
Item [57], ABSTRACT,
Line 10, after formula (A), delete "ethan-1,2-oxy-1,2-yl" and insert
-- ethan-1-oxy-1-yl --.

Signed and Sealed this

Ninth Day of September, 2003

JAMES E. ROGAN
*Director of the United States Patent and Trademark Office*